(12) United States Patent
Erenstone

(10) Patent No.: US 10,905,568 B2
(45) Date of Patent: Feb. 2, 2021

(54) PROSTHETIC LIMB SOCKET WITH VARIABLE HARDNESS

(71) Applicant: PVA MEDICAL, LLC, Cohoes, NY (US)

(72) Inventor: Jeffrey L. Erenstone, Lake Placid, NY (US)

(73) Assignee: PVA MEDICAL, LLC, Cohoes, NY (US)

( * ) Notice: Subject to any disclaimer, the term of this patent is extended or adjusted under 35 U.S.C. 154(b) by 111 days.

(21) Appl. No.: 15/444,841

(22) Filed: Feb. 28, 2017

(65) Prior Publication Data

US 2017/0246013 A1 Aug. 31, 2017

Related U.S. Application Data

(60) Provisional application No. 62/301,363, filed on Feb. 29, 2016.

(51) Int. Cl.
*A61F 2/50* (2006.01)
*B33Y 10/00* (2015.01)
(Continued)

(52) U.S. Cl.
CPC ............. *A61F 2/5046* (2013.01); *A61F 2/80* (2013.01); *B29C 64/386* (2017.08); *B33Y 10/00* (2014.12); *B33Y 50/00* (2014.12); *B33Y 50/02* (2014.12); *B33Y 80/00* (2014.12); *A61F 2/7812* (2013.01); *A61F 2002/505* (2013.01);
(Continued)

(58) Field of Classification Search
CPC .... A61F 2/5046; A61F 2/80; A61F 2002/505; A61F 2002/5047; A61F 2002/5049; A61F 2/7812; A61F 2/76; A61F 2002/5027; A61F 2002/30563; A61F 2002/30578; A61F 2002/30581; A61F 2002/30688; A61F 2002/5007; A61F 2002/5024; A61F 2002/5026; A61F 2002/503; A61F 2002/5032; A61F 2002/5036; A61F 2002/5043; A61F 2007/0051; B33Y 80/00; B33Y 50/00; B33Y 10/00; B33Y 70/00;
(Continued)

(56) References Cited

U.S. PATENT DOCUMENTS

| 4,923,475 A | 5/1990 | Gosthnian et al. |
| 5,050,090 A * | 9/1991 | Golub .................... G06Q 10/08 414/273 |

(Continued)

OTHER PUBLICATIONS

International Search Report Form PCT/ISA/220, International Application No. PCT/US/2017/019878, pp. 1-5, International Filing Date Feb. 28, 2017, search report dated Jun. 5, 2017.

*Primary Examiner* — Darrin D Dunn
(74) *Attorney, Agent, or Firm* — Schmeiser, Olsen & Watts, LLP

(57) ABSTRACT

A system and method for producing a customized prosthetic socket based on a digital representation of a residual limb that is used to form a digital model of a prosthetic socket. The digital model is customized to alter its internal structure to produce differing areas of flexibility and support while maintaining the overall geometry of the model and without having to use different materials. The digital model is converted for use with a three-dimensional printing or manufacturing device and then used to print the customized socket.

17 Claims, 8 Drawing Sheets

(51) Int. Cl.
| | |
|---|---|
| B29C 64/386 | (2017.01) |
| B33Y 50/00 | (2015.01) |
| B33Y 50/02 | (2015.01) |
| B33Y 80/00 | (2015.01) |
| A61F 2/80 | (2006.01) |
| A61F 2/78 | (2006.01) |
| G05B 19/4099 | (2006.01) |
| B29L 31/00 | (2006.01) |

(52) U.S. Cl.
CPC ............... *A61F 2002/5049* (2013.01); *A61F 2002/5053* (2013.01); *A61F 2002/5056* (2013.01); *B29L 2031/7532* (2013.01); *G05B 19/4099* (2013.01); *G05B 2219/35134* (2013.01); *G05B 2219/49007* (2013.01)

(58) Field of Classification Search
CPC ....... G06F 17/50; G06F 19/00; B29C 64/386; B29C 64/00
See application file for complete search history.

(56) References Cited

U.S. PATENT DOCUMENTS

| | | | | |
|---|---|---|---|---|
| 5,444,881 | A * | 8/1995 | Landi | A61G 5/1043 5/708 |
| 5,496,610 | A * | 3/1996 | Landi | B29C 53/04 428/73 |
| 5,522,402 | A * | 6/1996 | Cooley | A61B 5/1077 600/595 |
| 5,539,649 | A * | 7/1996 | Walsh | A61F 2/5046 623/901 |
| 5,552,992 | A * | 9/1996 | Hunter | G05B 19/4099 345/420 |
| 6,068,659 | A * | 5/2000 | O'Brien, Jr. | G06F 30/18 703/2 |
| 6,136,039 | A * | 10/2000 | Kristinsson | A61F 2/7812 623/36 |
| 6,177,034 | B1 * | 1/2001 | Ferrone | A61F 2/5046 264/40.1 |
| 7,162,322 | B2 * | 1/2007 | Arbogast | A61F 2/5046 700/118 |
| 7,611,476 | B2 * | 11/2009 | Taranow | A61F 5/01 602/12 |
| 7,937,973 | B2 | 5/2011 | Sorensen et al. | |
| 8,173,268 | B2 * | 5/2012 | Maus | B23K 1/0014 428/593 |
| 8,175,734 | B2 * | 5/2012 | Fogel | G06F 17/50 700/119 |
| 8,366,789 | B2 | 2/2013 | Summit | |
| 8,423,167 | B2 * | 4/2013 | Sanders | A61F 2/5046 623/901 |
| 9,072,463 | B2 * | 7/2015 | Sanders | A61B 5/1038 |
| 9,283,660 | B1 * | 3/2016 | Dignam | B23Q 1/25 |
| 9,469,075 | B2 * | 10/2016 | Zachariasen | A61F 2/6607 |
| 9,480,581 | B2 * | 11/2016 | Layman | A61F 2/5046 |
| 9,636,238 | B2 * | 5/2017 | Sanders | A61F 2/76 |
| 9,782,274 | B2 * | 10/2017 | Summit | A61F 2/5046 |
| 2004/0068337 | A1 * | 4/2004 | Watson | A61F 2/5046 700/98 |
| 2004/0260402 | A1 * | 12/2004 | Baldini | A61F 2/5046 623/33 |
| 2005/0145563 | A1 * | 7/2005 | Boyd | C02F 3/006 210/601 |
| 2006/0020348 | A1 * | 1/2006 | Slemker | A61B 5/107 623/33 |
| 2006/0105135 | A1 * | 5/2006 | Chien | B32B 3/12 428/73 |
| 2006/0123542 | A1 * | 6/2006 | Wilson | A47C 19/021 5/400 |
| 2007/0080479 | A1 * | 4/2007 | Arbogast | A61F 2/5046 264/222 |
| 2008/0155735 | A1 * | 7/2008 | Ferrara | A01N 25/18 2/412 |
| 2008/0161963 | A1 * | 7/2008 | Slemker | A61B 5/107 700/118 |
| 2010/0023149 | A1 * | 1/2010 | Sanders | A61F 2/5046 700/98 |
| 2010/0030083 | A1 * | 2/2010 | Sanders | A61B 5/0048 600/474 |
| 2010/0161076 | A1 * | 6/2010 | Pallari | A61F 2/5046 623/36 |
| 2011/0004335 | A1 * | 1/2011 | Summit | A61F 2/5046 700/119 |
| 2011/0082578 | A1 * | 4/2011 | Stanhope | G01B 5/008 700/98 |
| 2011/0126973 | A1 * | 6/2011 | Andrewlavage, Jr. | B28B 19/0038 156/247 |
| 2011/0241240 | A1 * | 10/2011 | Gothait | B29C 64/245 264/40.6 |
| 2012/0022657 | A1 * | 1/2012 | Iannotti | A61F 2/30942 623/18.11 |
| 2012/0116539 | A1 * | 5/2012 | Armstrong | A61F 2/5046 623/36 |
| 2012/0143077 | A1 * | 6/2012 | Sanders | A61B 5/0535 600/547 |
| 2013/0052398 | A1 * | 2/2013 | Dean | B21D 47/00 428/80 |
| 2013/0124151 | A1 * | 5/2013 | Mech | G06F 17/50 703/1 |
| 2013/0150981 | A1 * | 6/2013 | Summit | A61F 2/60 623/33 |
| 2013/0226533 | A1 * | 8/2013 | Summit | A61F 2/5046 703/1 |
| 2014/0088929 | A1 * | 3/2014 | Suttin, Sr. | G06F 17/50 703/1 |
| 2014/0149082 | A1 * | 5/2014 | Sanders | A61F 2/76 703/1 |
| 2014/0163697 | A1 * | 6/2014 | Sanders | A61F 2/5046 623/36 |
| 2014/0173812 | A1 * | 6/2014 | Krueger | A42B 3/122 2/455 |
| 2014/0188260 | A1 * | 7/2014 | Layman | A61F 2/5046 700/98 |
| 2014/0228860 | A1 * | 8/2014 | Steines | A61F 2/30942 606/130 |
| 2014/0288670 | A1 * | 9/2014 | Phillips | A61F 2/68 623/36 |
| 2014/0316526 | A1 * | 10/2014 | Grotz | A61L 27/54 623/20.17 |
| 2015/0142150 | A1 * | 5/2015 | Layman | A61F 2/5046 700/98 |
| 2015/0278414 | A1 * | 10/2015 | Zhou | G06F 30/23 703/2 |
| 2015/0297369 | A1 * | 10/2015 | Mosler | A61F 2/7812 623/36 |
| 2015/0328840 | A1 * | 11/2015 | Zachariasen | A61F 2/6607 700/98 |
| 2015/0359644 | A1 * | 12/2015 | Sanders | A61F 2/7812 623/34 |
| 2016/0058519 | A1 | 3/2016 | Herr | |
| 2016/0331563 | A1 * | 11/2016 | Kane | A61F 2/76 |
| 2017/0161405 | A1 * | 6/2017 | Ishizuka | G06F 17/5004 |
| 2017/0174346 | A1 * | 6/2017 | Wilson | B64D 11/0647 |
| 2017/0246013 | A1 * | 8/2017 | Erenstone | B33Y 50/00 |
| 2017/0290685 | A1 * | 10/2017 | Montez | A61F 2/76 |
| 2017/0323037 | A1 * | 11/2017 | Schroeder | A61F 2/30 |
| 2017/0360578 | A1 * | 12/2017 | Shin | G09B 23/286 |
| 2018/0098865 | A1 * | 4/2018 | Mojica | A61B 5/742 |
| 2018/0235779 | A1 * | 8/2018 | Dudding | A61F 2/5046 |
| 2018/0243111 | A1 * | 8/2018 | Hand | A61F 2/80 |
| 2018/0243112 | A1 * | 8/2018 | Hand | A61F 2/80 |

* cited by examiner

PROSTHETIC LIMB SOCKET WITH VARIABLE HARDNESS

CROSS-REFERENCE TO RELATED APPLICATIONS

The present application claims priority to U.S. Provisional Application No. 62/301,363, filed on Feb. 29, 2016.

BACKGROUND OF THE INVENTION

1. Field of the Invention

The present invention relates to artificial limb sockets and, more specifically, to a system and method for creating sockets with variable hardness for an improved custom fit.

2. Description of the Related Art

The major component of the interface between the residual (remaining) limb of an amputee and their prosthetic device is called the socket. The socket bears the weight of the body of the user and distributes the load across the prosthesis. Because the shape and structure of each residual limb varies between patients, every socket must be custom made by a certified and licensed practitioner so that it properly fits a patient. Despite the customization of sockets by professionals, traditional prosthetic socket manufacturing does not always allow for the proper distribution of pressure between the residual limb and the prosthetic device. As a result, a poorly designed socket does not distribute pressure properly and will often cause pain or injuries. Additionally, current methods of manufacturing prosthetics are expensive and labor intensive. Accordingly, there is a need in the art for a system and method of designing and manufacturing prosthetic device sockets that improve the fit of the socket while reducing the time and expense associated with manufacturing the improved socket.

BRIEF SUMMARY OF THE INVENTION

The present invention comprises a system and method of producing a prosthetic limb socket using computer-aided design (CAD), computer-aided engineering (CAE), and computer assisted manufacturing (CAM) so that prosthetic practitioners (prosthetists) can design and manufacture custom flexible inner prosthetic supports that better interface with individual amputees and more evenly distribute pressure. More specifically, a system for producing a prosthetic socket according to the present invention includes a data acquisition module configured to form a digital representation of a residual limb from an input of patient data, a computer design module configured to create a digital model of a prosthetic socket having an internal structure based on the digital representation of the residual limb and to allow a user to modify the digital model to adjust the internal structure to change at least a portion of the internal structure of the digital model, and print conversion module associated with the computer design module that is configured to receive the modified digital model from the computer design module and convert the modified digital model into instructions for a manufacturing device. The invention may further comprise a manufacturing device, such as computer-assisted manufacturing machine, that is associated with the print conversion module for receiving the converted modified digital model and for forming a prosthetic socket that corresponds to the modified digital model. The data acquisition module may be configured to receive the input of patent patient data from a three-dimensional scanner used to take a three-dimensional scan of the residual limb or a three-dimensional scan of a cast of the residual limb. The data acquisition module may also be configured to receive the input of patient data from a practitioner that has measured the residual limb. The computer design module may comprise computer aided design software, and the computer design module may be G-code software.

The present invention also includes a method of producing a prosthetic socket, comprising the steps of acquiring data representing coordinates of a residual limb, forming a digital representation of the residual limb based on the acquired data, creating a digital model of a prosthetic socket having in internal structure based on the digital representation of the residual limb, allowing modifications to the digital model to adjust the internal structure to change at least a portion of the internal structure of the digital model, and converting the modified digital model into instructions for a manufacturing device. The method may additionally include the step of forming an actual prosthetic socket that corresponds to the modified digital model.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
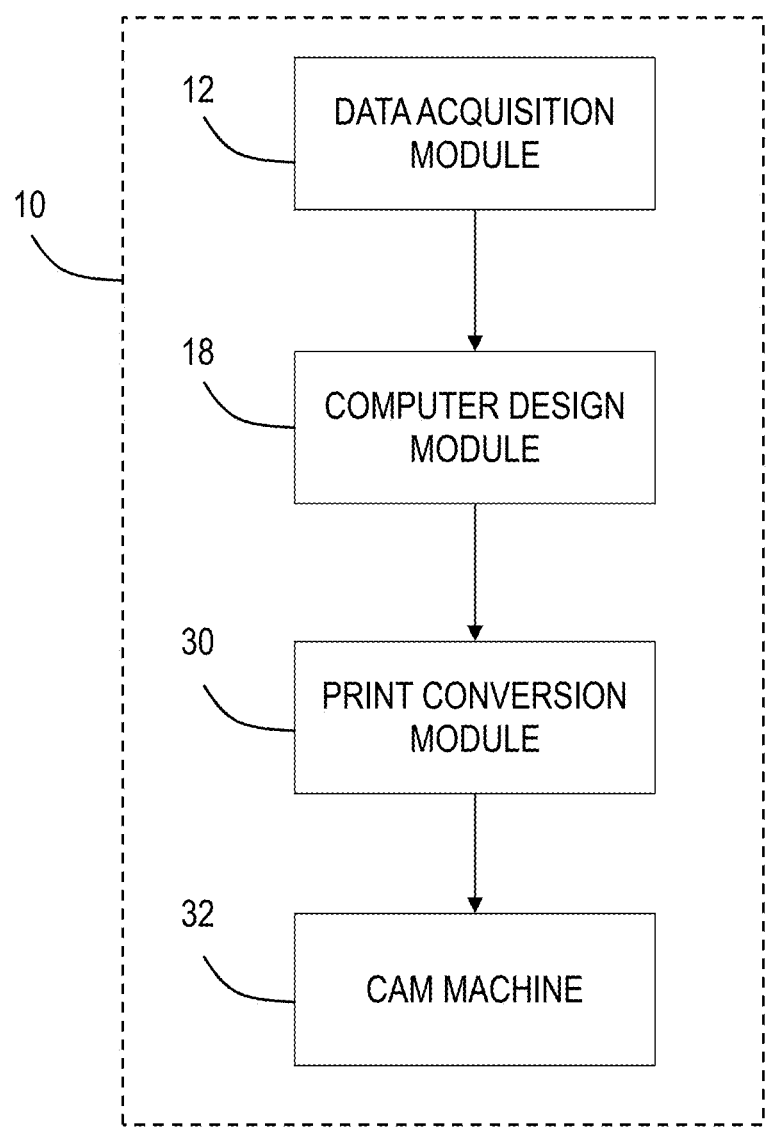
FIG. 1 is a schematic of a system for designing and producing an improved prosthetic socket according to the present invention.
Figure 2:
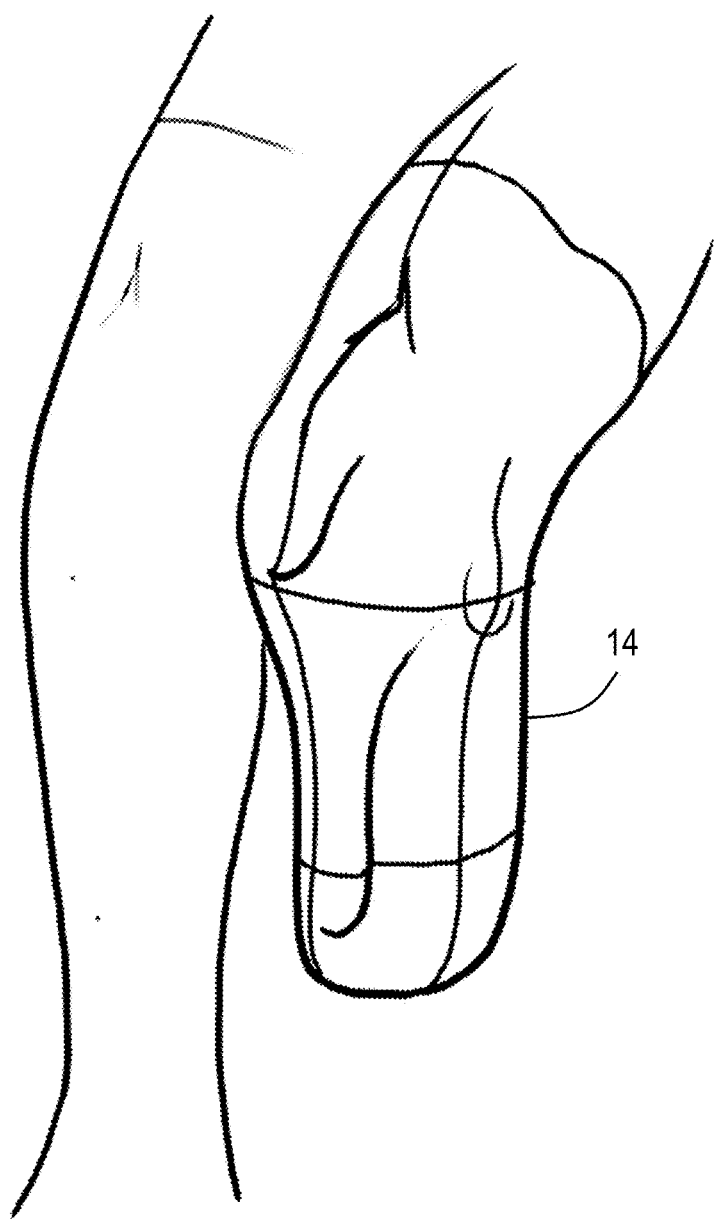
FIG. 2 is a perspective view of a patient residual limb according to the present invention
Figure 3:
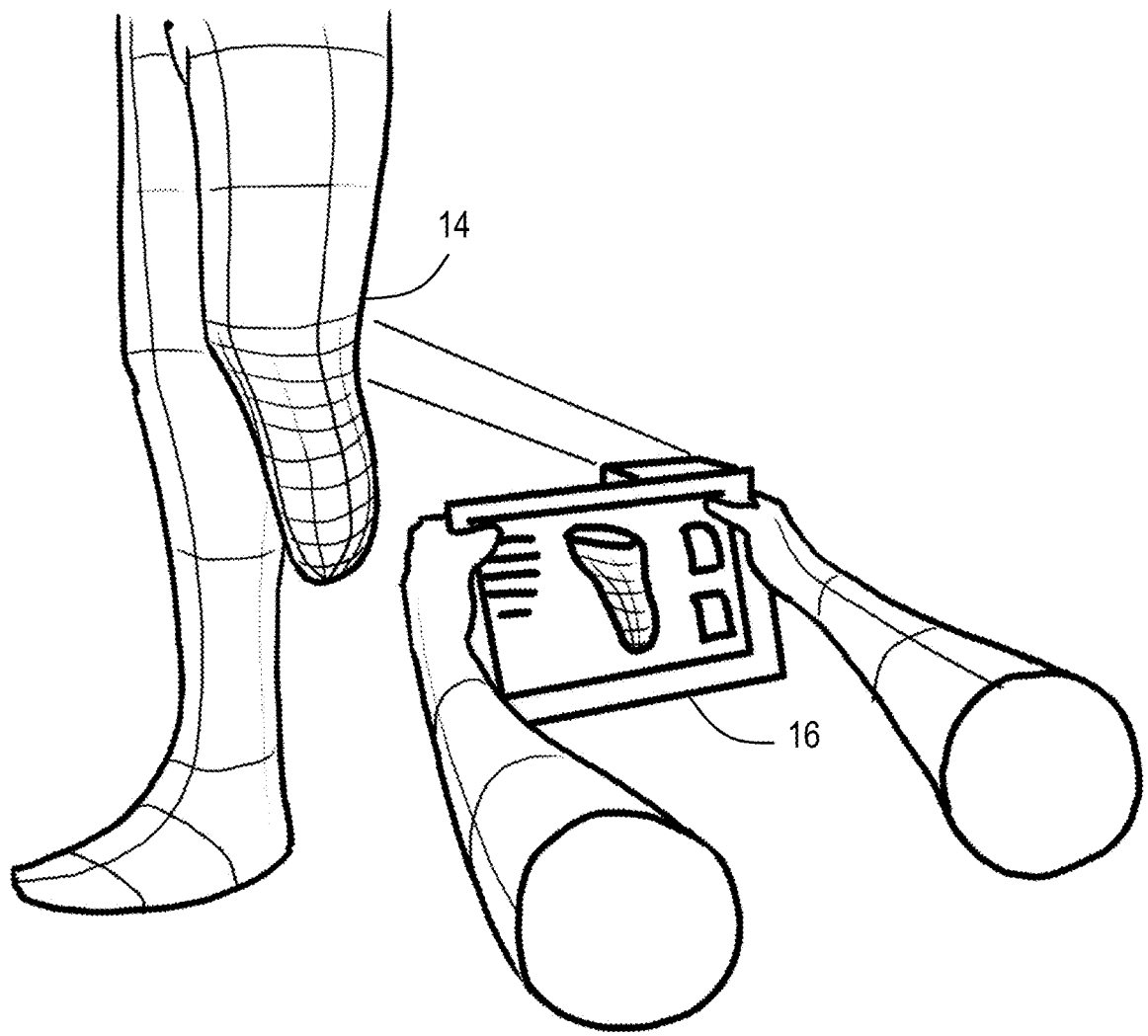
FIG. 3 is a perspective view of the collection of patient residual limb data using a three-dimensional scanner according to the present invention.

Referring to the figures, wherein like numerals refer to like parts throughout, there is seen in FIG. 1, a prosthetic socket design system 10 comprising a patient data acquisition module 12 that is configured to acquire the specific anthropomorphic data of a patient having a residual limb 14 to be outfitted with a prosthetic device, as seen in FIG. 2. Data acquisition module 12 may comprise a digital scanner 16 that acquires patient anthropomorphic data via 3D digital scanning that acquires the coordinates of the bones, fatty tissues, and muscles of the residual limb to be outfitted with the socket and prosthetic device, as seen in FIG. 3. Data acquisition module 12 is configured to digitize the coordinates into a shapefile (digital mold) through use of conventional scanning software. Data acquisition module 12 may alternatively or additionally be configured to acquire patient anthropomorphic data through the digitization of a physical mold. For example, a user may acquire the exact coordinates of a residual limb from a plaster cast of that residual limb using the same 3D scanning process described above and then digitize those coordinates into a shapefile. Data acquisition module 12 may alternatively or additionally be configured to acquire patient anthropomorphic data that is obtained by a user manually measuring predetermined set of coordinates and then entering the coordinates into data acquisition module 12 so that the digital shapefile can be generated.

Figure 4:
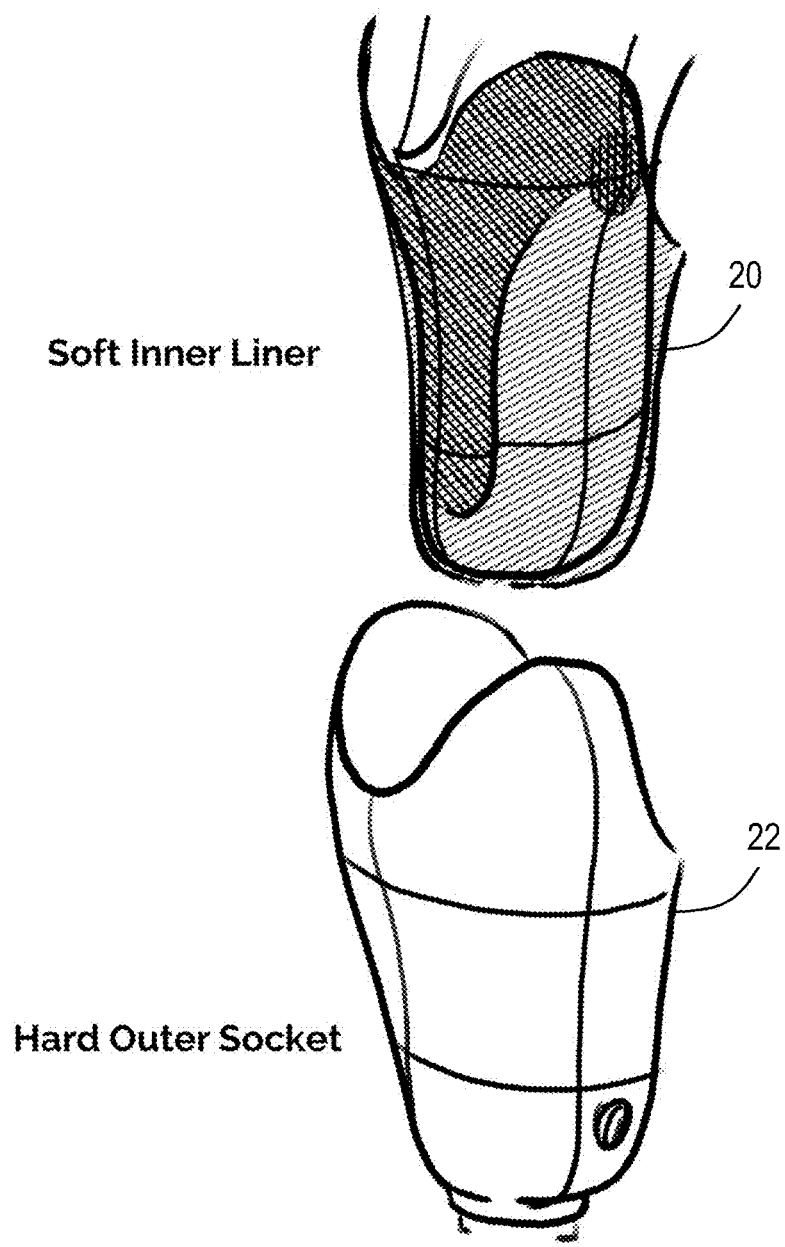
FIG. 4 is perspective view of a prosthetic device having an inner socket modified according to the present invention.
Figure 5:
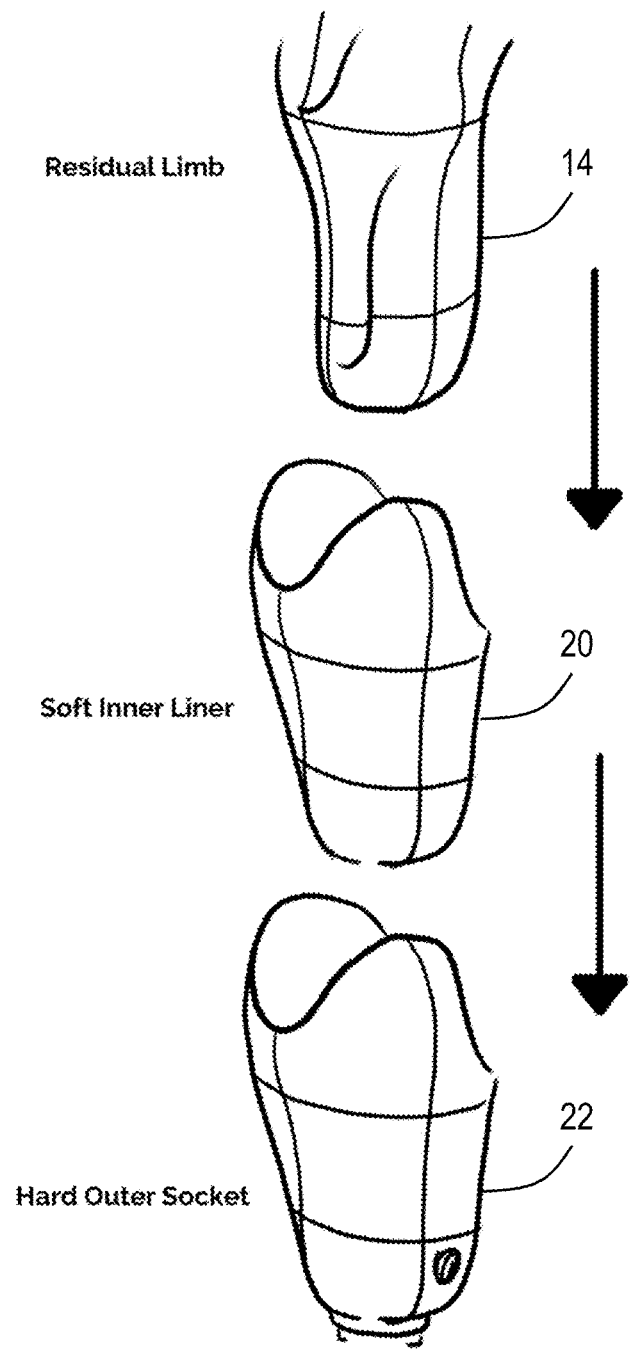
FIG. 5 is a schematic of the attachment of an outer and inner socket to a patient limb according to the present invention.
Figure 6:
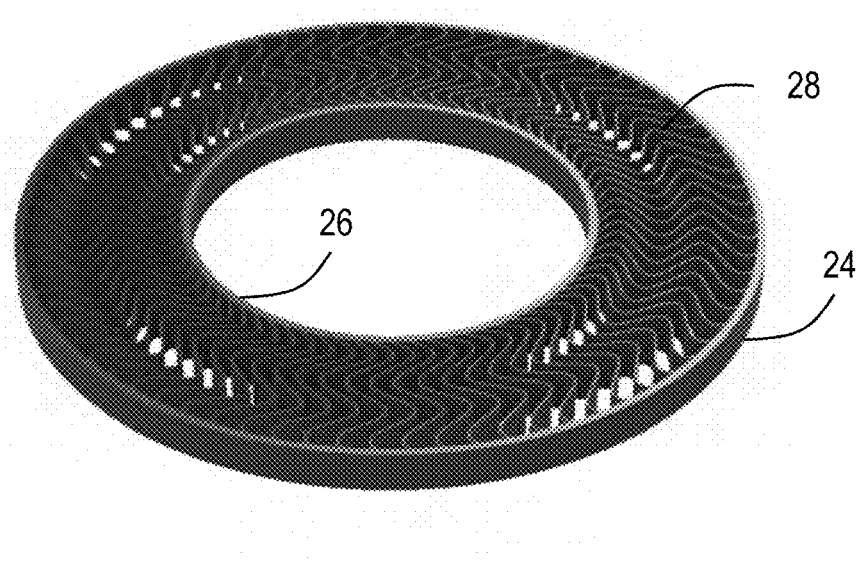
FIG. 6 is a perspective view of a cross-section of an inner socket according to the present invention.
Figure 7:
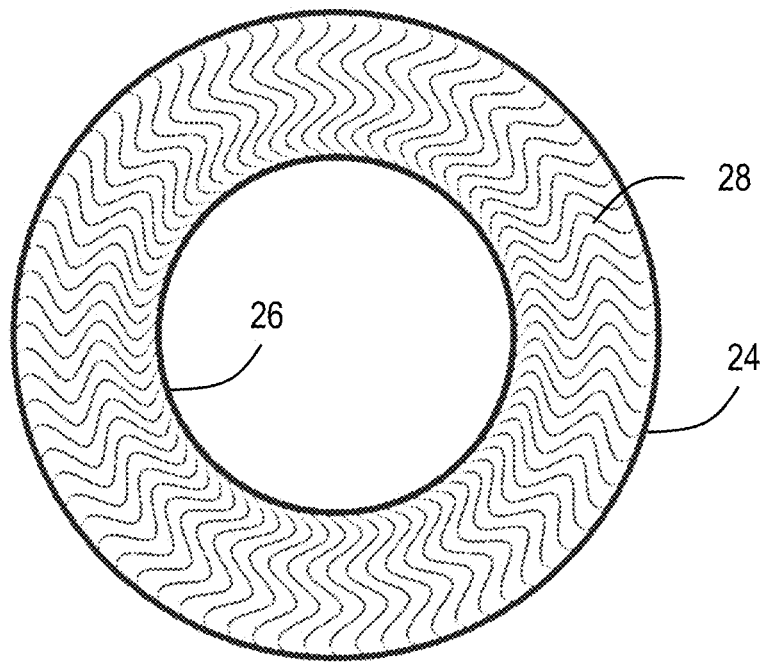
FIG. 7 is a cross-sectional view of an inner socket according to the present invention.

System 10 further comprises a computer design module 18 interconnected to data acquisition module 12 and configured to receive the shapefile once is has been generated. Computer design module 18 may comprise CAD/CAE software that is configured for the present invention. More specifically, computer design module 18 is programmed to display the shapefile for the practitioner and allow the practitioner to enter a desired offset (distance between the residual limb and flexible inner socket) and thickness defining a flexible inner socket 20 as seen in FIG. 4. Inner socket 20 is used as a liner between limb 14 and the hard outer socket 22 of a prosthetic when attaching to limb 14 as seen in FIG. 5. Based upon the user selected offset and thickness, computer design module 18 generates a digital representation of a model socket that can be further manipulated by the practitioner as described herein. Computer design module 18 preferably assigns a default uniform density to the internal structure of the digital socket (the flexible internal supports of the socket) that may then be manipulated by the practitioner. Computer design module 18 is further configured to allow the practitioner to assign areas of the digital socket for increased density of the internal architecture structure. Areas with higher density are used to reduce pressure points that form proximately to any sensitive areas of a residual limb that require lower density areas. Practitioners use their training, expertise, and experience to identify areas on each residual limb that require different levels of density and then use computer design module 18 to make these customized changes to the digital socket and thus the digital shapefile. Referring to FIGS. 6 and 7, an exemplary inner socket 20 according to the present invention may have an outer surface 24 and an inner surface 26 spaced apart by internal structural elements 28, all of which are formed from a single material, such as a polymer or plastic. The number of structural elements 28 may thus be varied to change the flexibility of inner socket 20 while maintaining the same outer geometry. While socket 20 is shown with sinusoidal or triangular wave element (zigzag) structural elements 28, it should be recognized that other shapes may be used if they provide structural stability between outer surface 24 and inner surface 26 and are able to be provided in various densities or amounts.

System 10 further comprises a print conversion module 30 interconnected to computer design module 18 and configured to receive the customized digital shape file. Print conversion module 30 is programmed to convert the digital shapefile into an appropriate file format for computer-assisted manufacturing or three-dimensional (3D) printing. For example, print conversion module 30 may be programmed to convert digital shape file into G-code, a conventional language used to determine the optimal settings of a computer-assisted manufacturing (CAM) machine (or 3D printer). The printing file format, such G-code, is used to determine the extrusion material temperature of the particular machine, the extrusion rate/speed, the build plate temperature, and the tool path (movement of the extruder to form the shape and internal architecture structure of the socket). Print conversion module 30 thus translates the customized shapefile into the corresponding instructions for manufacturing a socket based on the customized shapefile. This process is frequently referred to as slicing and involves the translation of 3D models into instructions that a 3D printer can understand and can be optimized to the particular 3D printer to be used.

Figure 8:
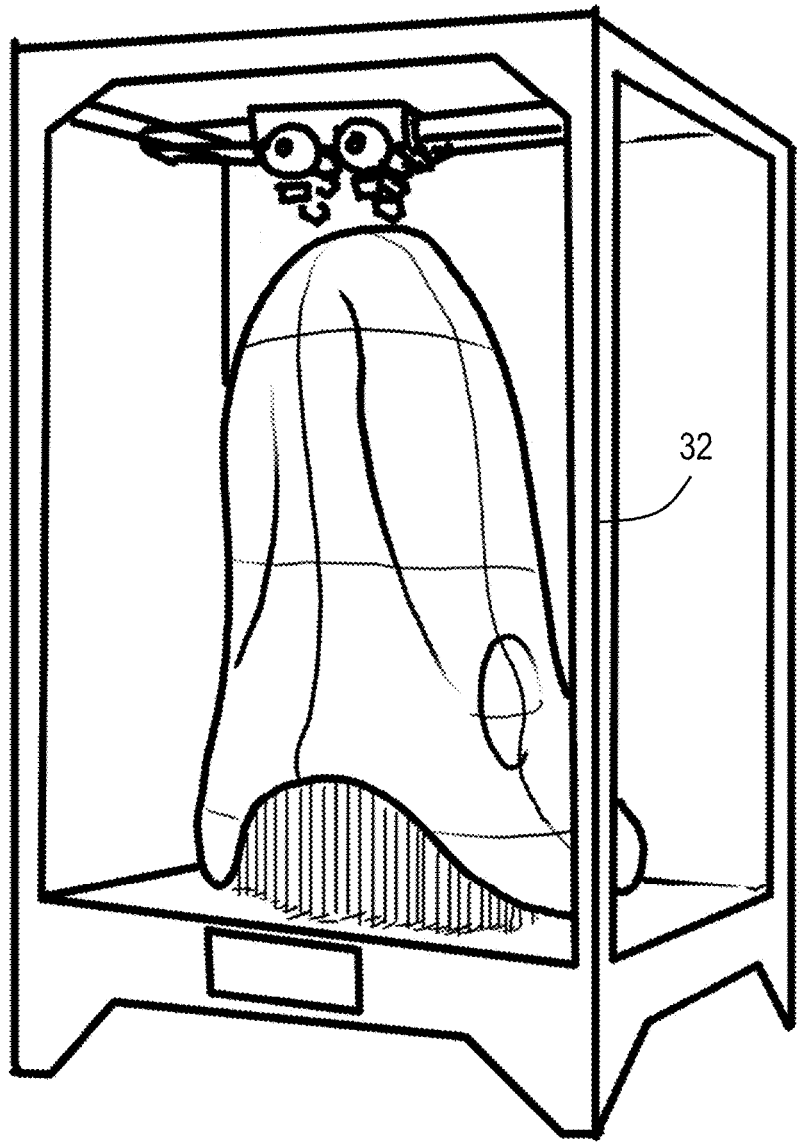
FIG. 8 is a perspective view of a computer-assisted manufacturing machine (3D printer) making an inner socket according to the present invention.

System 10 additionally comprises a CAM machine 32 associated with print conversion module 30 that is configured to manufacture a socket based on the customized shapefile that has been converted into the appropriate language for CAM machine 32 by conversion module 30. For example, CAM machine 32 may use the G-Code produced by print conversion module 30 to fabricate a flexible inner socket as designed by the practitioner using computer design module 18. CAM machine 32 thus uses the G-code specifications and tool paths to physically fabricate an inner socket 20, as seen in FIG. 8. As an example, the Raise3D N2 Plus printer available from Raise3D, Inc. of Santa Clara, Calif. may be used as CAM machine 32.

System 10 may thus be used to produce an artificial limb inner socket that is digitally designed to vary the forces applied to the residual limb for pressure-sensitive and tolerant areas. Moreover, system 10 can produce an inner socket from a single material while maintaining a uniform thickness within the socket yet having variable durometers to address pressure-sensitive and tolerant areas. System 10 makes it easy to control, adjust, and modulate socket pressures and, at the same time, does not require any increased volume of the inner socket, increased weight of the socket, or the use of multiple materials. While system 10 is best used for inner socket design and manufacturing, system 10 could be used for outer socket 22 design as well as for any other medical device or prosthetic element that would benefit from a customized patient fit.

Figure 9:
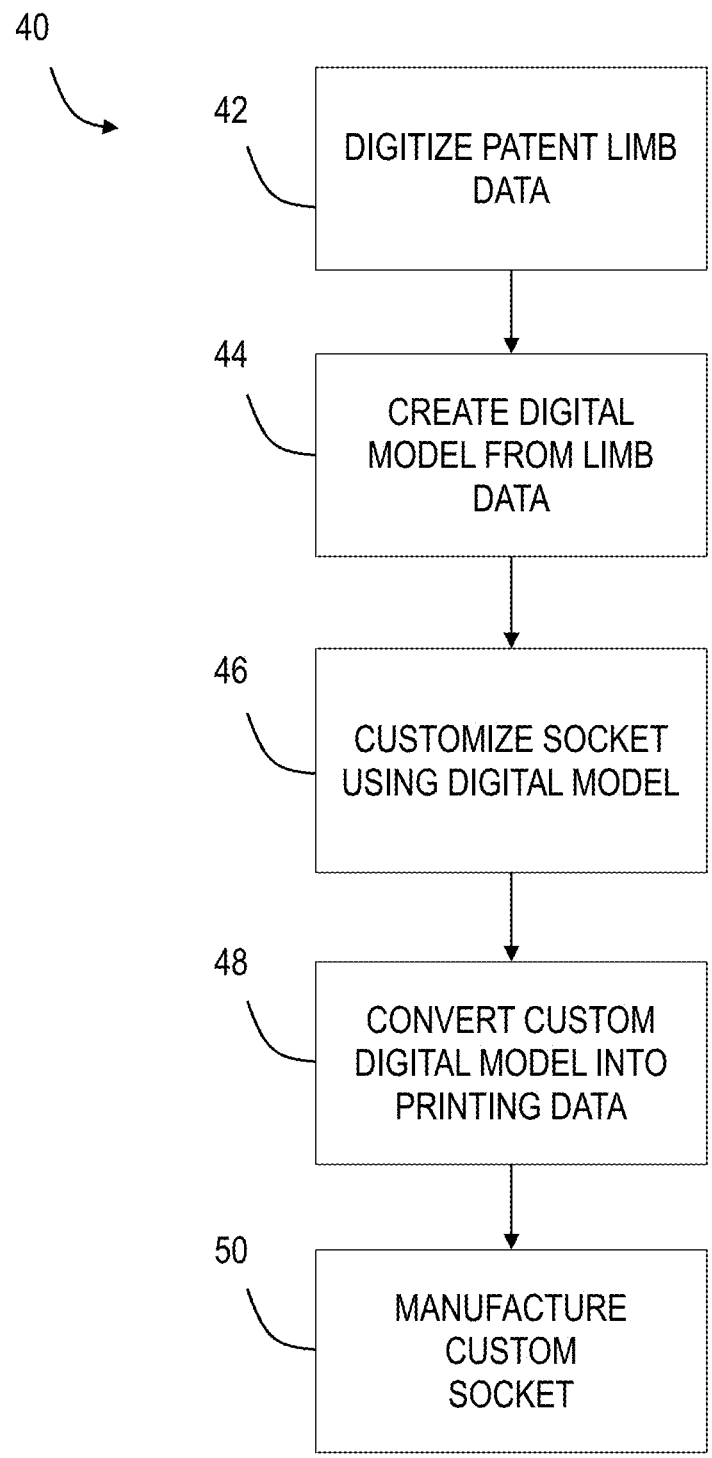
FIG. 9 is a flowchart of a process for designing and producing an improved prosthetic socket according to the present invention.

Referring to FIG. 9, a prosthetic socket manufacturing process 40 according to the present invention begins with the step of digitizing the specific anthropomorphic data of the residual limb of a patient 42. The three preferred approaches of performing this step are digitally scanning the residual limb, digitally scanning a physical cast of the limb, or manually measuring the residual limb and entering the measurements. Next, the scanned data is used to create a digital model 44. Conventional software can be used to develop the digital model, including directly from a 3D/structural scanner if used in step 42. Once the digital model is created 44, a qualified user may then use CAD or computer-aided engineering (CAE) software to develop a customized socket from the digital model 46. As discussed above, this step involves the generation of a default model socket and then adjustment of that model based upon practitioner inputs to develop an ideal internal architecture structure that has variable internal density and thus flexibility to correspond to a particular residual limb. Once the digital model has been customized at step 46, the customized digital model is converted into an appropriate language or protocol for manufacturing by a 3D printer or CAM machine 48. As described above, an acceptable conventional language is G-code and accounts for the particular machine/filament combination, ideal extrusion temperature, extrusion rate/speed, build plate temperature, and tool path of the CAM machine. It should be recognized that the present invention may be used for various types of orthoses, braces, furniture, and protective clothing. Finally, the custom socket is manufactured by CAM machine 50.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A method comprising:
   receiving data representing coordinates of a shape of a residual limb of a patient;
   forming a model of a flexible inner socket based upon the received data, the flexible inner socket configured to be disposed between the residual limb of the patient and a hard outer socket;
   receiving, as input, a thickness and an offset of the model of the flexible inner socket;
   assigning a default uniform density to an internal structure of the model of the flexible inner socket;
   assigning areas of the model of the flexible inner socket for varying density from the default uniform density of the internal structure by identifying areas on a model of the residual limb;
   modifying the internal structure based on the assigned areas of the model of the flexible inner socket to provide a modified model of the flexible inner socket having a modified internal structure, wherein the internal structure comprises a plurality of internal structural elements, each of the plurality of internal structural elements extending outward from an inner surface of the flexible inner socket to an outer surface of the flexible inner socket, wherein the inner surface is proximal to the residual limb and the outer surface is distal to the residual limb, further wherein the modifying includes adding or removing internal structural elements to vary a density of the flexible inner socket while maintaining an outer geometry of the flexible inner socket having the thickness; and
   creating a data file comprising the modified model of the flexible inner socket having the thickness, the offset, and the assigned areas of modified internal structure for use in manufacturing the flexible inner socket.

2. The method as recited in claim 1, wherein the outer geometry is defined by a uniform thickness of the model of the flexible inner socket that is unchanged as a function of the density being varied.

3. The method as recited in claim 1, wherein modifying the internal structure comprises varying the number of internal structural elements.

4. The method as recited in claim 3, wherein modifying the internal structure comprises varying the number internal structural elements extending between the inner surface and the outer surface.

5. The method as recited in claim 4, wherein the number of internal structural elements extending between an inner surface of the model and an outer surface comprises one of sinusoidal wave elements and triangular wave elements.

6. The method as recited in claim 1, wherein modifying the internal structure comprises increasing the density of the internal structure.

7. The method as recited in claim 1, wherein modifying the internal structure comprises modifying the internal structure to vary an internal density.

8. The method as recited in claim 1, wherein modifying the internal structure comprises modifying the internal structure to vary durometer.

9. The method as recited in claim 1, wherein modifying the internal structure comprises modifying the internal structure to vary hardness.

10. The method as recited in claim 1, wherein a material of the model is not varied as a function of the modifying of the internal structure.

11. The method as recited in claim 1, wherein receiving data representing coordinates of the shape of the residual limb of the patient is practiced by one of digital scanning of the residual limb, digital scanning of a physical mold of the residual limb, and manually measuring the residual limb.

12. The method as recited in claim 1, further comprising manufacturing the flexible inner socket using the data file comprising the modified model.

13. The method as recited in claim 12, wherein the manufacturing comprises 3D printing.

14. A prosthetic flexible inner socket formed by the method of claim 1.

15. The method as recited in claim 1, wherein assigning the default uniform density to the internal structure of the model of the flexible inner socket comprises assigning the default uniform density to the internal structure of an entire model of the flexible inner socket.

16. A computing system comprising:
   a processor configured to:
   receive data representing coordinates of a shape of a residual limb of a patient; and
   receive the data representing the residual limb from the data acquisition model and form a model of a flexible inner socket, the flexible inner socket configured to be disposed between the residual limb of the patient and a hard outer socket;
   receive, as input, a thickness and an offset of the flexible inner socket and to assign a default uniform density to an internal structure of the model of the flexible inner socket;
   receive input assigning areas of the internal structure of the model of the flexible inner socket for varying the default uniform density of the internal structure of the model;
   modify the internal structure of the assigned areas of the model to vary a density of the internal structure to create a modified model of the flexible inner socket, wherein the internal structure comprises a plurality of internal structural elements, each of the plurality of internal structural elements extending outward from an inner surface of the model to an outer surface of the model, wherein the inner surface is proximal to the residual limb and the outer surface is distal to the residual limb, further wherein the modifying includes adding or removing internal structural elements to vary the density of the flexible inner socket while maintaining an outer geometry of the flexible inner socket having the desired thickness; and create a data file comprising the modified model of the flexible inner socket having the thickness, and the offset, and the assigned areas of the internal structure having varying density for use in forming the flexible inner socket.

17. A method for forming a prosthetic socket, the method comprising:

receiving data representing coordinates of a shape of a residual limb of a patient;

forming a model of a flexible inner socket based upon the received data, the flexible inner socket configured to be disposed between the residual limb of the patient and a hard outer socket;

receiving, as input, a thickness and an offset of the model of the flexible inner socket;

assigning a default uniform density to an internal structure of the model of the flexible inner socket;

assigning areas of the model of the flexible inner socket for varying density from the default uniform density of the internal structure by identifying areas on a model of the residual limb;

modifying the internal structure based on the assigned areas of the model of the flexible inner socket to provide a modified model of the flexible inner socket having a modified internal structure, wherein the internal structure comprises a plurality of internal structural elements, each of the plurality of internal structural elements extending outward from an inner surface of the model to an outer surface of the model, wherein the inner surface is proximal to the residual limb and the outer surface is distal to the residual limb, wherein the number of internal structural elements, extending between the proximal inner surface of the model and the distal outer surface, have a curved external surface and each of the plurality of internal structural elements are spaced apart by a distance, wherein the varying the density of corresponding areas of the model of the socket comprises changing the distance between each of the internal structural elements and the number of internal structural elements in the corresponding areas of the model of the socket, further wherein the modifying includes adding or removing internal structural elements to vary a density of the flexible inner socket while maintaining an outer geometry of the flexible inner socket having the desired thickness; and creating a data file comprising the modified model of the flexible inner socket having the thickness, the offset, and the assigned areas of modified internal structure for use in manufacturing the flexible inner socket.

* * * * *